US00PP15896P3

(12) United States Plant Patent
van der Voort

(10) Patent No.: US PP15,896 P3
(45) Date of Patent: Jul. 26, 2005

(54) LILY PLANT NAMED 'SIMPLON'

(50) Latin Name: *Lilium L.*
Varietal Denomination: Simplon

(75) Inventor: Cees A. van der Voort, Katwijk (NL)

(73) Assignee: Vletter & Den Haan Beheer B.V. (NL)

( * ) Notice: Subject to any disclaimer, the term of this patent is extended or adjusted under 35 U.S.C. 154(b) by 0 days.

(21) Appl. No.: 09/357,100

(22) Filed: Jul. 19, 1999

(65) Prior Publication Data

US 2002/0069443 P1 Jun. 6, 2002

(51) Int. Cl.[7] ..... A01H 5/00
(52) U.S. Cl. ..... Plt./315
(58) Field of Search ..... Plt./315

(56) References Cited

PUBLICATIONS

UPOV–ROM GTITM Computer Database 2000/02, GTI Jouve Retrieval Software, citations for 'Simplon'.*
UPOV–ROM GTITM Computer Database 2000/02, GTI Jouve Retrieval Software, citation for 'Simplon', 1995.*
NL Plant Breeder's Rights application LEL 1095; grant date May 16, 1995.
BE Plant Breeder's Rights application 25124; filing date Sep. 22, 1995.
FR Plant Breeder's Rights application 0158504; filing date Sep. 4, 1995.
PL Plant Breeder's Rights application LIO0040; filing date Dec. 4, 1995.
DE Plant Breeder's Rights application LIU00082; filing date Sep. 6, 1995.
ZA Plant Breeder's Rights application PT 2661; grant date Sep. 1, 2000.

* cited by examiner

*Primary Examiner*—Anne Marie Grunberg
(74) *Attorney, Agent, or Firm*—Foley & Lardner, LLP

(57) ABSTRACT

A new and distinct cultivar of Lily plant named 'Simplon' characterized by having large, upright flowers, white flower color, contrasting reddish brown pollen, and vigorous growth habit.

1 Drawing Sheet

1

BACKGROUND OF THE INVENTION

The present invention comprises a new and distinct cultivar of lily plant, botanically known as *Lilium L.,* and hereinafter referred to by the cultivar name 'Simplon'.

'Simplon' is a product of a planned breeding program which had the objective of creating new lily cultivars having large, white, upright flowers and vigorous growth.

'Simplon' was originated from a hybridization made by the inventor in a controlled breeding program in Rijnsburg, the Netherlands in 1984. The male and female parents were unnamed seedlings of *Lilium L.* oriental hybrids. Both parents are proprietary cultivars used in the breeding program.

'Simplon' was discovered and selected as one flowering plant within the progeny of a stated cross by the inventor, Cees A. van der Voort, on Jun. 7, 1984 in a controlled environment in Rijnsburg, the Netherlands.

The first act of asexual reproduction of 'Simplon' was accomplished when scales were taken from the initial selection in October, 1987 in a controlled environment in Rijnsburg, the Netherlands by, or under the supervision of, Cees A. van der Voort. Horticultural examination of selected units initiated May 1987 has demonstrated that the combination of characteristics as herein disclosed for 'Simplon' are firmly fixed and are retained through successive generations of asexual reproduction.

2

BRIEF DESCRIPTION OF THE INVENTION

The following traits have been repeatedly observed and are determined to be basic characteristics of 'Simplon' which in combination distinguish this lily as a new and distinct cultivar:

1. large, upright flowers;
2. white flower color;
3. contrasting reddish brown pollen; and
4. vigorous growth habit.

'Simplon' has not been observed under all possible environmental conditions. The phenotype of the new cultivar may vary significantly with variations in environment such as temperature, light intensity, and daylength without any change in genotype. The following observations, measurements, and comparisons describe plants grown in the experimental research station CPRO-DLO, Wageningen, the Netherlands under conditions which approximate those generally used in commercial practice.

Of the many commercial cultivars known to the present inventor, no other cultivars are similar in comparison to 'Simplon'.

BRIEF DESCRIPTION OF THE DRAWING

The accompanying color photographic drawing shows typical plant and flower characteristics of 'Simplon', with colors being as true as possible with illustrations of this type.

DETAILED BOTANICAL DESCRIPTION

In the following description, color references are made to The Royal Horticultural Society Colour Chart (R.H.S.). The color values were determined between 12 am and 2 pm at the Dutch experimental research station CPRO-DLO, Wageningen, the Netherlands.

Origin: Seedling from breeding program.

Parentage:

*Female parent.*—Unnamed seedling.

*Male parent.*—Unnamed seedling.

Classification:

*Botanical.*—A hybrid of the genus *Lilium L.*

*Commercial.*—Oriental Lily cv. 'Simplon'.

Plant:

*Form.*—A single stem carrying numerous, alternately arranged pedicels.

*Height.*—Medium to high for the mature plant, approximately 90 cm, depending on cultivation conditions.

*Growth habit.*—Vigorous: from the start of vegetation to the beginning of the first flowering takes 90 days depending on cultivation conditions; approximately 20–30% more vigorous than the traditional 'Stargazer' cultivar.

*Stem.*—Circular in transverse section; anthocyanin pigmentation absent; internodal length 5.5 cm, depending on the cultivation conditions of the cultivar.

*Foliage.*—Quantity: Approximately 70, depending on cultivation conditions. Size of leaf: Mature leaves are 10 cm long and 3.5 cm wide, depending on cultivation conditions. Shape of leaf: Generally ovate, hardly any pubescence. Color: Light green RHS 136C.

*Bulb.*—Size: 16 to 18 cm in circumference. Color: White.

Bud:

*Form.*—Tapering like a lancet.

*Size.*—Large, 14 cm in length, depending on cultivation conditions.

*Opening.*—Unfolds normally.

*Color.*—White, RHS 155D, just before opening.

*Tepals.*—Folded, three visible.

Flower:

*Blooming habit.*—Raceme.

*Size.*—Medium to wide, 21 cm in diameter, depending on cultivation conditions.

*Borne.*—Upright to horizontal along a longitudinal axis.

*Shape.*—Generally, hexagonal star in form and bowl-shaped in cross-section.

*Tepalage.*—Number of Tepals: 6. Arrangement: Three inner and three outer. Color: Upper Surface: White, RHS 155D; color of mid-vein is green RHS 145B, mid-vein is visible only in the inner thoat. Lower Surface: White, RHS 155D. Spotting or Marking: None.

*Pedicel.*—Length: Medium to long. Color: RHS 135D. Form: Tapering like a lancet.

*Texture.*—Papillose.

*Disease resistance.*—Average in comparison to the disease resistance level of traditional lily cultivars.

*Fragrance.*—Absent.

*Lasting quality.*—Excellent; i.e., the average lasting period is at least 21 days, when cut and kept in a controlled climate in conformity with Dutch Auctions and Research Station standards.

Reproductive organs:

*Stamens and anthers.*—Arrangements: Anthers form a generally circular pattern at their upper ends. Number: 6. Length: 8 cm, depending on cultivation conditions. Filament Color: Yellow-green 149D.

*Pollen color.*—Reddish-brown, RHS 171B.

*Anther color.*—Reddish-brown RHS 171D.

*Pistils.*—Green RHS 145B.

*Stigma.*—Purple RHS 185C.

*Ovaries.*—Triangular in shape.

I claim:

1. A new and distinct cultivar of Lily plant named 'Simplon' having a vigorous growth habitat and upright, white flowers, as illustrated and described herein.

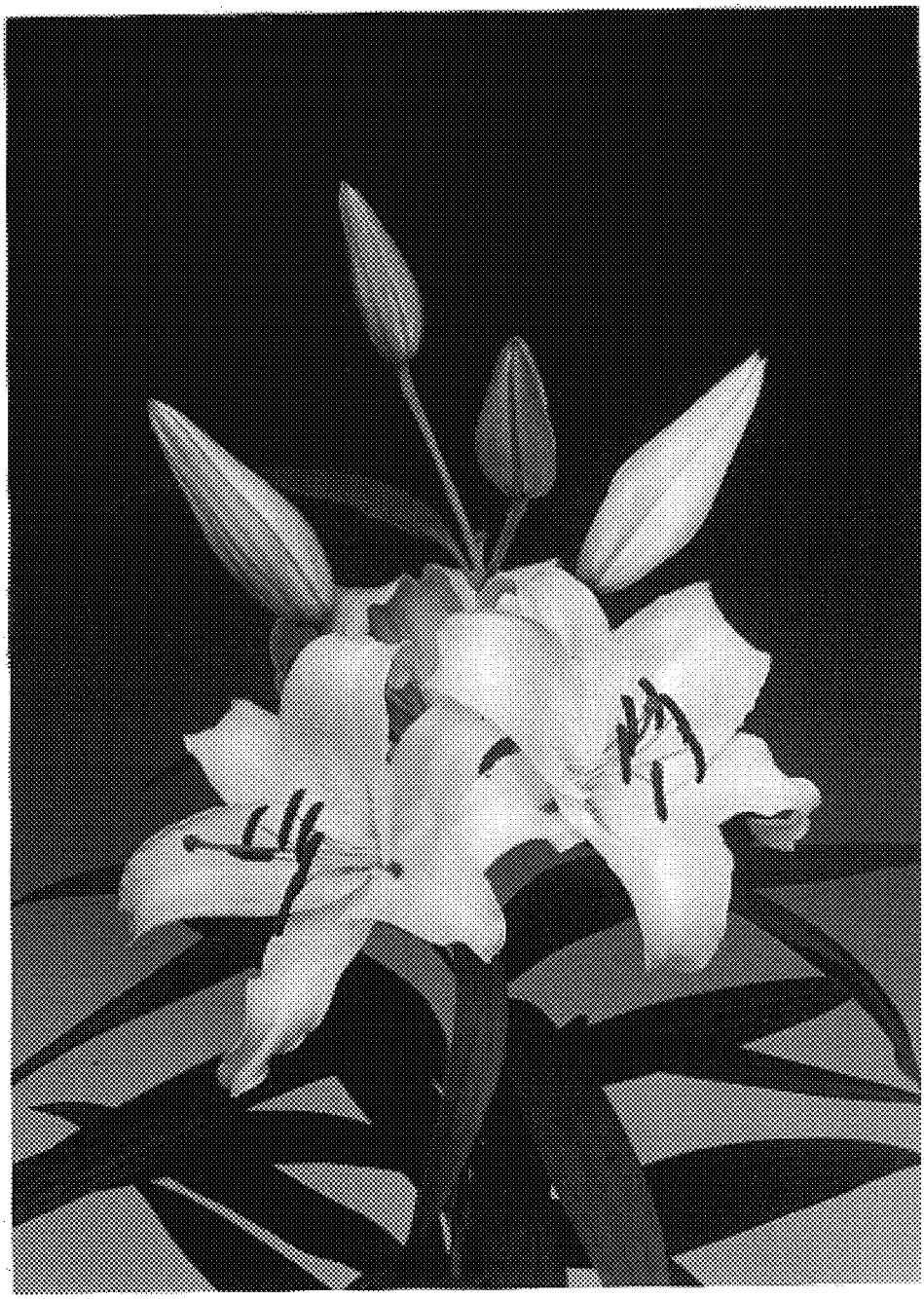

* * * * *